United States Patent [19]

Ling et al.

[11] 4,273,756

[45] Jun. 16, 1981

[54] IMMUNOASSAY FOR CLASS SPECIFIC ANTIBODIES

[75] Inventors: Chung-Mei Ling, Antioch; Richard H. Decker; Ruben Chairez, both of Deerfield, all of Ill.

[73] Assignee: Abbott Laboratories, North Chicago, Ill.

[21] Appl. No.: 928,651

[22] Filed: Jul. 28, 1978

[51] Int. Cl.² .................... G01N 33/16; A61K 39/00; A61K 43/00
[52] U.S. Cl. .................................... 424/1; 23/230 B; 424/12
[58] Field of Search .................... 424/1, 12; 23/230 B

[56] References Cited

U.S. PATENT DOCUMENTS

| | | | |
|---|---|---|---|
| 3,720,760 | 3/1973 | Bennich et al. | 424/1 |
| 3,904,367 | 9/1975 | Golibersuch | 23/230 B |
| 3,941,876 | 3/1976 | Marinkovich | 424/1 |
| 3,959,650 | 5/1976 | Lukens, Jr. | 421/1 |
| 4,020,151 | 4/1977 | Bolz et al. | 424/1.5 |
| 4,031,197 | 6/1977 | Marinkovich | 424/1 |
| 4,048,298 | 9/1977 | Niswender | 424/1.5 |

OTHER PUBLICATIONS

Diment et al., Affinity Chromatography, Hoffmann–Ostenhof et al., Ed., Pergamon Press, NY, 1978, pp. 229–231.
Jacoby et al., Journal of Immunological Methods, 11, (1976), pp. 37–48.
Bradley et al., J. of Clinical Microbiology, vol. 5, No. 5, May, 1977, pp. 521–530.

*Primary Examiner*—Benjamin R. Padgett
*Assistant Examiner*—Christine M. Nucker
*Attorney, Agent, or Firm*—John J. McDonnell

[57] ABSTRACT

The present invention encompasses a method for determining a class specific antibody to an antigen comprising:

(a) binding an antibody for a specific immunoglobulin class to a solid support to form a class specific antibody reagent;
(b) reacting the class specific antibody reagent with test sample;
(c) removing unbound test sample to provide an antigen reagent, and
(d) reacting the antigen reagent with a known antigen and measuring the amount of bound antigen thereby determining the amount of class specific antibody to that antigen.

The present invention is useful for differential diagnosis, since the relative amount of class specific antibodies varies with the progress of infection.

18 Claims, 2 Drawing Figures

IMMUNOASSAY FOR CLASS SPECIFIC ANTIBODIES

BACKGROUND OF THE INVENTION

The immunoglobulin molecule consists of one or more sets of four polypeptide chains, two heavy chains molecular weight about 53,000 and two light chains molecular weight about 22,000, joined by disulfide bonds.

Five classes of immunoglobulin are distinguished by the presence of heavy-chain antigenic determinants, which are designated by the lower case Greek characters corresponding to the Roman letters applied to the immunoglobulins:

| IMMUNOGLOBULIN | HEAVY-CHAIN ANTIGENIC DETERMINANT | |
|---|---|---|
| IgG | γ | (gamma) |
| IgA | α | (alpha) |
| IgM | μ | (mu) |
| IgD | δ | (delta) |
| IgE | ε | (epsilon) |

There are also subclasses of IgG, IgA, and IgM, based upon other antigenic determinants, which are designated by numerals (e.g., γ1, α1, μ1). Four subclasses of IgG have been recognized, two of IgA, and two of IgM. All subclasses are found in the sera of all normal individuals.

IgG is the most abundant immunoglobulin in the serum of normal humans. It is also found in the tissue fluids, and it can cross the placenta from the maternal to the fetal circulations. It has antibacterial, antiviral, and antitoxic activities in vivo, and in vitro. It is a late responding antibody.

IgM is characterized by possession of heavy chains with the amino acid sequence that defines the antigenic determinant μ. A distinguishing feature of IgM function is its strong cytolytic and complement-fixing activity, which far exceeds that of IgG. IgM is usually the first antibody to appear in animals or humans following immunization. It is then gradually replaced by IgG.

IgA is the second most abundant immunoglobulin in human serum and is the chief secretory immunoglobulin. It is useful in antibacterial and respiratory viral defense.

IgE is the least abundant immunoglobulin. It has skin sensitizing properties and is responsible for a variety of bronchial, gastrointestinal, skin and other allergic reactions.

Very little is known about the structure and biological function of IgD. IgD antibodies have been found in patients sensitive to cow's milk and patients with systemic lupus erythematosus.

Methods for isolating the above immunoglobulin classes are well-known. Methods for raising antibodies to immunoglobulins are also known and methods for binding immunoglobulins to solid supports are known. Methods for isolating antigens, labeling antigen with fluorescent molecules, radioactive molecules or enzymes to permit measuring bound antigen are well-known. There are likewise, indirect methods for measuring bound antigen, such as reacting the bound antigen with a labeled (radioactive, fluorescent, enzyme) antibody to the antigen.

U.S. Pat. No. 4,020,151 describes an immunoassay for IgG, IgA, and IgM concentrations in the serum which comprises first reacting a solid support with test sample to adsorb IgG, IgA, IgM and then reacting a labeled antibody to IgG, IgA or IgM and measuring the bound antibody.

Bradley et al., Journal of Clinical Microbiology, May 1977, pages 521-530, describes the determination of IgG and IgM related to hepatitis A virus by radioimmunoassay. Antibody to hepatitis A virus in the test specimen was coated on a polyvinyl surface by reacting the polyvinyl surface with test serum. Purified hepatitis A antigen and $^{125}I$ labeled immunoglobulin G (IgG), that is, anti-hepatitis A antibody, were subsequently reacted sequentially with the polyvinyl surface. Counting $^{125}I$ bound to the well provided a determination of total anti-hepatitis A in test serum. Immunoglobulin M anti-hepatitis A was distinguished depending on whether the above anti-hepatitis A reactiion was inhibited by a goat anti-IgM. It is important to be able to distinguish antibodies to specific immunoglobulins since, for example, in hepatitis A infection, IgM antibodies are prevalent in the acute stage of the infection and IgG is prevalent in the convalescent stage. A large portion of the population have been exposed to hepatitis A and it is necessary to distinguish acute versus convalescent stage of infection, i.e., IgM versus IgG antibodies. The present invention provides a unique method for monitoring class specific antibodies during bacterial and viral infection as well as allergic reactions.

DETAILED DESCRIPTION OF THE INVENTION

Figure 1:
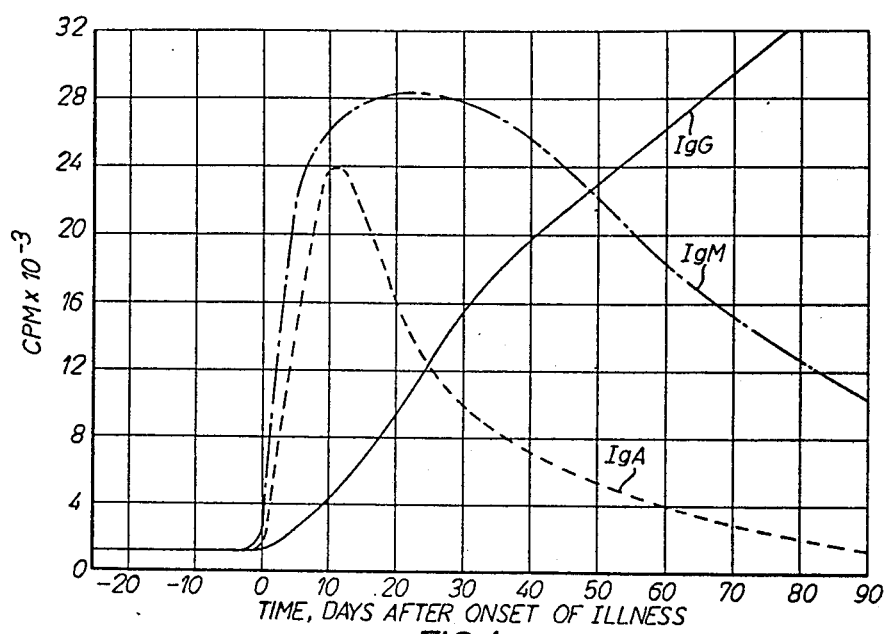
FIG. 1-Composite graph of class specific antibodies IgG, IgM and IgA having anti-hepatitis A activity shown as time in days after onset of illness versus counts per minute $(CPM) \times 10^{-3}$.

The present invention encompasses a method for determining a class specific antibody to an antigen comprising:

(a) binding an antibody for a specific immunoglobulin class to a solid support to form a class specific antibody reagent;

(b) reacting the class specific antibody reagent with test sample;

(c) removing unbound test sample to provide an antigen reagent, and (d) reacting the antigen reagent with a known antigen and measuring the amount of bound antigen thereby determining the amount of class specific antibody to the known antigen.

In the context of this invention specific immunoglobulin class refers to IgG, IgM, IgA, IgE and IgD.

Solid support refers to insoluble polymeric material sorptive for the antibody. Known materials of this type include hydrocarbon polymer such as polystyrene, polyethylene, polypropylene, polybutylene, butyl rubber and other synthetic rubbers. Other suitable organic polymers include silastic rubber, polyesters, polyamides, cellulose and cellulosic derivatives, acrylates, methacrylates, and vinyl polymers such as vinyl chloride, and polyvinyl fluoride. Copolymers such as graft copolymers of polystyrene are also useful. In addition to the foregoing materials, the solid support surface may comprise silica gel, silicone wafers, glass insoluble protein metals and the solid support may be in the form of beads, tubes, strips disk and the like.

The term antibody to a specific immunoglobulin class is exemplified by an antibody specific for μ-chain of human IgM, α-chain of human IgA, γ-chain of human IgG, δ-chain of human IgD, and ε-chain of human IgE raised in a non-human species such as rabbit, goat, horse, sheep, guinea pig, etc.

Class specific antibody reagents are solid supports coated with non-human species (anti-μ chain of human IgM), solid supports with non-human species (anti-α chain of human IgA), solid supports with non-human species (anti-γ chain of human IgG), solid supports with non-human species (anti-δ chain of human IgD), solid supports with non-human species (anti-ε chain of human IgE), such as polystyrene beads coated with goat (anti-μ chain of human IgM), polystyrene beads coated with goat (anti-γ chain of human IgG), or polystyrene beads coated with goat anti-α chain of human IgA.

Antiserum containing class specific antibodies diluted in buffer is incubated with the plastic beads and the beads are washed with water and dried to provide a class specific antibody reagent. This class specific antibody reagent is incubated with diluted solution of human test serum and washed with water to remove unbound immunoglobulins in the test sample. Thus, class specific immunoglobulins, including those present in the serum because of infection and which contain antibodies to the infecting agent will adhere to the bead thereby forming an antigen reagent for binding the antigen which is reactive with the class specific antibody present in the serum. Typical antigen reagents are:

solid support coated with non-human species (anti-μ chain of human IgM) having IgM from test sample bound thereto, solid support coated with non-human species (anti-α chain of human IgA) having IgA from test sample bound thereto, solid support coated with non-human species (anti-γ chain of human IgG) having IgG from test sample bound thereto, solid support coated with non-human species (anti-δ chain of human IgD) having IgD from test sample bound thereto, solid support coated with non-human species (anti-ε chain of human IgE) having IgE from test sample bound thereto.

The antigen reagent is reacted with a known antigen. The amount of antigen bound reflects the amount of class specific antibody to that antigen. The antigen may be directly labeled by conventional fluorescent dyes, enzymes, or radioactive labels to permit determination of the amount bound, or it may be indirectly labeled by further reaction, for example, with an antibody to the antigen which is labeled with fluorescent dyes, enzymes or radioactive labels by conventional methods. Antigens and antibodies labeled directly are known:

antibody or antigen-$^{125}$I, Biochem. J., 89:114, 1963;
antibody or antigen-Horseradish peroxidase, J. Cytochem. Histochem., Vol 22, pp. 1084, 1974;
antibody or antigen-Fluorescence, Diagnostic Procedures for Viral and Rickettsial Infection, chapt 4, page 179, 1969.

In the case of an antigen already labeled, the antigen reagent is reacted with labeled antigen, washed to remove unbound labeled antigen and the amount of antigen bound is determined by conventional enzyme, fluorometric or radiochemical techniques.

In the case of unlabeled antigen, the unlabeled antigen is reacted with the antigen reagent, washed to remove unbound antigen, subsequently reacted with a labeled antibody to the antigen, and the label of the antibody is measured.

The following examples illustrate the present invention and are not intended to limit it in spirit or scope.

EXAMPLE I

1. Solutions of goat antiserum specific for: (a) μ-chains of human IgM; (b) α-chains of human IgA; and (c) γ-chains of human IgG, were prepared each at 1:1000 in 0.01 M Tris, pH 9.0. Solutions were used to coat 6 mm polystyrene beads overnight at room temperature, and each set of beads was washed and air-dried and stored at 4° C. until used.

2. Specimens of a series of serums from a subject with hepatitis A and negative control specimens were diluted 1,000 fold in 50% calf serum, 0.2% Tween-20 and 0.005 M EDTA in phosphate buffered saline (PBS).

3. Two tenths of the diluted specimens were each incubated in duplicate overnight at room temperature with anti-μ, anti-α, anti-γ beads, and beads were washed 2 times with 5 ml H$_2$O.

4. Beads were incubated overnight at room temperature with 0.2 ml of hepatitis A virus (HAV) from HAV positive liver extract diluted 1:40 in PBS). Beads were again washed two times with 5 ml H$_2$O.

5. Beads were incubated with 0.2 ml of anti-HAV $^{125}$I in 50% fetal calf serum, 0.2% Tween-20, 0.005 M EDTA and 5% normal human serum and were washed 2 times with 5 ml H$_2$O.

6. Beads were transferred to plastic tubes and counted in a γ-counter. Count rates of each set were plotted vs. the days that the specimens were collected relative to onset of illness from hepatitis A, FIG. 1.

EXAMPLE II

1. Anti-μ, anti-α and anti-γ beads were prepared as in Example 1, step 1.

2. Specimens of a series of serums from a subject with hepatitis B and negative control specimens were diluted 1:1000 in normal goat serum.

Figure 2:
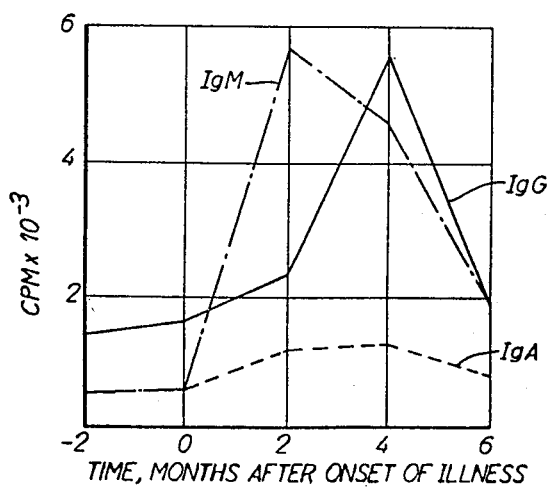
FIG. 2-Anti-hepatitis B core activity in class specific antibodies IgG, IgM and IgA shown as month after onset of illness versus counts per minute $(CPM) \times 10^{-3}$.

3. Two tenths of the diluted specimens were incubated in duplicate overnight at room temperature with anti-μ beads, anti-α beads and anti-γ beads, and all beads were washed 2 times with 5 ml H$_2$O. 4. Beads were incubated overnight at room temperature with 0.2 ml of HBcAg (purified hepatitis B core antigen or HBcAg, diluted 1:50 in a diluent of 1% Bovine Serum Albumin (BSA), 1% Tween-20, 1% normal human serum, 0.01 M Tris, and 0.005 M EDTA in saline, pH 7.2, and were washed 2 times with 5 ml H$_2$O. 5. Beads were incubated overnight at room temperature with anti-HBcAg $^{125}$I in a diluent of 25% calf serum, 12.5% normal goat serum, 12.5% normal rabbit serum and 0.5% normal human serum in PBS and were washed 2 times with 5 ml H$_2$O. 6. Beads were transferred to plastic tubes and counted in a γ-counter. Count rates of each set (anti-μ, anti-α and anti-γ were plotted vs. the days that the specimens were collected relative to the approximate onset of hepatitis B, FIG. 2.

EXAMPLE III

Hepatitis B surface antigen directly labeled with $^{125}I$ by the methods of Greenwood, et al. produced similar results as Example II.

EXAMPLE IV

Horseradish peroxidase labeled hepatitis A antigen labeled by the methods of Journal of Cystochemistry, Histochemistry Vol. 22, page 1084 (1974), produces similar results as Example I.

What is claimed is:

1. A method for determining a class specific antibody to an antigen comprising:
   (a) binding an antibody for a specific immunoglobulin class to a solid support to provide a class specific antibody reagent;
   (b) reacting the class specific antibody reagent with test sample;
   (c) removing unbound test sample to provide an antigen reagent;
   (d) reacting the antigen reagent with a known labeled antigen, and
   (e) removing unbound labeled antigen and measuring the amount of bound labeled antigen, thereby determining the amount of class specific antibody to the known antigen.

2. A method, according to claim 1, for determining IgM antibody to hepatitis A virus antigen comprising:
   (a) binding non-human species anti-$\mu$ chain of IgM antibody to a solid support to provide a class specific antibody reagent;
   (b) reacting the class specific antibody reagent with test sample and washing to remove unbound test sample and provide an antigen reagent;
   (c) reacting the antigen reagent with labeled hepatitis A virus antigen and washing to remove unbound labeled hepatitis A virus antigen, and
   (d) measuring bound labeled hepatitis A virus antigen.

3. A method according to claim 1, for determining IgG antibody to hepatitis A virus antigen comprising:
   (a) binding non-human species anti-$\gamma$ chain of IgG antibody to a solid support to provide a class specific antibody reagent;
   (b) reacting the class specific antibody reagent with test sample and washing to remove unbound test sample to provide an antigen reagent;
   (c) reacting the antigen reagent with labeled hepatitis A virus antigen and washing to remove unbound labeled hepatitis A virus antigen, and
   (d) measuring bound labeled hepatitis A virus antigen.

4. A method, according to claim 1, for determining IgA antibody to labeled hepatitis A antigen comprising:
   (a) binding non-human species anti-$\alpha$ chain of IgA antibody to a solid support to provide a class specific antibody reagent;
   (b) reacting the class specific antibody reagent with test sample and washing to remove unbound test sample and provide an antigen reagent;
   (c) reacting the antigen reagent with labeled hepatitis A antigen and washing to remove unbound labeled hepatitis A antigen, and
   (d) measuring bound labeled hepatitis A antigen.

5. A method according to claim 1, for determining IgG antibody to hepatitis B antigen comprising:
   (a) binding non-human species anti-$\gamma$ chain of IgG antibody to a solid support to provide a class specific antibody reagent;
   (b) reacting the class specific antibody reagent with test sample and washing to remove unbound test sample and provide an antigen reagent;
   (c) reacting the antigen reagent with labeled hepatitis B antigen and washing to remove unbound labeled hepatitis B antigen, and
   (d) measuring bound labeled hepatitis B antigen.

6. A method, according to claim 1, for determining IgM antibody to hepatitis B antigen comprising:
   (a) binding non-human species anti-$\mu$ chain of IgM antibody to a solid support to provide a class specific antibody reagent;
   (b) reacting the class specific antibody reagent with test sample and washing to remove unbound test sample to provide an antigen reagent;
   (c) reacting the antigen reagent with labeled hepatitis B antigen and washing to remove unbound labeled hepatitis B antigen, and
   (d) measuring bound labeled hepatitis B antigen.

7. A method according to claim 1, for determining IgA antibody to hepatitis B antigen comprising:
   (a) binding non-human species anti-$\alpha$ chain of IgA antibody to a solid support to provide a class specific antibody reagent;
   (b) reacting the class specific antibody reagent with test sample and washing to remove unbound test sample to provide an antigen reagent;
   (c) reacting the antigen reagent with labeled hepatitis B antigen and washing to remove unbound labeled hepatitis B antigen, and
   (d) measuring bound labeled hepatitis B antigen.

8. A method for determining a class specific antibody to an antigen comprising:
   (a) binding an antibody for a specific immunoglobulin class to a solid support to provide a class specific antibody reagent;
   (b) reacting the class specific antibody reagent with test sample;
   (c) removing unbound test sample to provide an antigen reagent;
   (d) reacting the antigen reagent with a known antigen;
   (e) removing unbound antigen; and
   (f) reacting the bound antigen with a labeled antibody to the known antigen, removing the unbound labeled antibody and determining the bound labeled antibody, thereby determining the amount of class specific antibody to the known antigen.

9. A method according to claim 8 for determining IgM antibody to hepatitis A virus antigen comprising:
   (a) binding non-human species anti-$\mu$ chain of IgM antibody to a solid support to provide a class specific antibody reagent;
   (b) reacting the class specific antibody reagent with test sample;
   (c) washing class specific antibody reagent reacted with test sample to provide an antigen reagent;
   (d) reacting the antigen reagent with hepatitis A virus antigen and washing with water to remove unbound hepatitis A virus antigen;
   (e) reacting the product of (d) with labeled antibody to hepatitis A virus antigen and washing to remove unbound labeled antibody, and
   (f) measuring the amount of bound labeled antibody.

10. A method according to claim 8 for determining IgA antibody to hepatitis A virus antigen comprising:
   (a) binding non-human species anti-α chain of IgA antibody to a solid support to provide a class specific antibody reagent;
   (b) reacting the class specific antibody reagent with test sample;
   (c) washing class specific antibody reagent reacted with test sample to provide an antigen reagent;
   (d) reacting the antigen reagent with hepatitis A virus antigen and washing with water to remove unbound hepatitis A virus angigen;
   (e) reacting the product of (d) with labeled antibody to hepatitis A virus antigen and washing to remove unbound labeled antibody, and
   (f) measuring the amount of bound labeled antibody.

11. A method according to claim 8 for determining IgG antibody to hepatitis A virus antigen comprising:
   (a) binding non-human species anti-γ chain of IgG, antibody to a solid support to provide a class specific antibody reagent;
   (b) reacting the class specific antibody reagent with test sample;
   (c) washing class specific antibody reagent reacted with test sample to provide an antigen reagent;
   (d) reacting the antigen reagent with hepatitis A virus antigen and washing with water to remove unbound hepatitis A virus antigen;
   (e) reacting the product of (d) with labeled antibody to hepatitis A virus and washing to remove unbound labeled antibody, and
   (f) measuring the amount of bound labeled antibody.

12. A method according to claim 8 for determining IgM antibody to hepatitis B virus antigen comprising:
   (a) binding non-human species anti-μ chain of IgM antibody to a solid support to provide a class specific antibody reagent;
   (b) reacting the class specific antibody reagent with test sample;
   (c) washing class specific antibody reagent reacted with test sample to provide an antigen reagent;
   (d) reacting the antigen reagent with hepatitis B virus antigen and washing with water to remove unbound hepatitis B virus antigen;
   (e) reacting the product of (d) with labeled antibody to hepatitis B virus antigen and washing to remove unbound labeled antibody, and
   (f) measuring the amount of bound labeled antibody.

13. A method according to claim 8 for determining IgA antibody to hepatitis B virus antigen comprising:
   (a) binding non-human species anti-α chain of IgA antibody to a solid support to provide a class specific antibody reagent;
   (b) reacting the class specific antibody reagent with test sample;
   (c) washing class specific antibody reagent reacted with test sample to provide an antigen reagent;
   (d) reacting the antigen reagent with hepatitis B virus antigen and washing with water to remove unbound hepatitis B virus antigen;
   (e) reacting the product of (d) with labeled anti-body to hepatitis B virus antigen and washing to remove unbound labeled antibody, and
   (f) measuring the amount of bound labeled antibody.

14. A method according to claim 8 for determining IgG antibody to hepatitis B virus antigen comprising:
   (a) binding non-human species anti-γ chain of IgG antibody to a solid support to provide a class specific antibody reagent;
   (b) reacting the class specific antibody reagent with test sample;
   (c) washing class specific antibody reagent reacted with test sample to provide an antigen reagent;
   (d) reacting the antigen reagent with hepatitis B virus antigen and washing with water to remove unbound hepatitis B virus antigen;
   (e) reacting the product of (d) with labeled antibody to hepatitis B virus antigen and washing to remove unbound labeled antibody, and
   (f) measuring the amount of bound labeled antibody.

15. An immunoassay reagent comprising a solid support coated with antibody specific for μ-chain of human IgM.

16. An immunoassay reagent comprising a solid support coated with antibody specific for α-chain of human IgA.

17. An immunoassay reagent comprising a solid support coated with antibody specific for δ-chain of human IgD.

18. An immunoassay reagent comprising a solid support coated with antibody specific for ε-chain of human IgE.

* * * * *